(12) United States Patent
Machida et al.

(10) Patent No.: US 12,730,116 B2
(45) Date of Patent: Sep. 8, 2026

(54) METHOD FOR REDUCING MEASUREMENT ERROR

(71) Applicant: SEKISUI MEDICAL CO., LTD., Tokyo (JP)

(72) Inventors: Satoshi Machida, Tokyo (JP); Hiroki Osako, Tokyo (JP); Kouji Yamamoto, Tokyo (JP); Yuuri Hayakawa, Tokyo (JP)

(73) Assignee: SEKISUI MEDICAL CO., LTD., Tokyo (JP)

( * ) Notice: Subject to any disclaimer, the term of this patent is extended or adjusted under 35 U.S.C. 154(b) by 652 days.

(21) Appl. No.: 18/025,813

(22) PCT Filed: Sep. 10, 2021

(86) PCT No.: PCT/JP2021/033235
§ 371 (c)(1),
(2) Date: Mar. 10, 2023

(87) PCT Pub. No.: WO2022/054890
PCT Pub. Date: Mar. 17, 2022

(65) Prior Publication Data

US 2023/0358767 A1 Nov. 9, 2023

(30) Foreign Application Priority Data

Sep. 11, 2020 (JP) ................................ 2020-152539

(51) Int. Cl.
*G01N 33/72* (2006.01)
*C07C 49/86* (2006.01)
*C12P 3/00* (2006.01)

(52) U.S. Cl.
CPC ........... *G01N 33/725* (2013.01); *C07C 49/86* (2013.01); *C12P 3/00* (2013.01); *G01N 2333/908* (2013.01)

(58) Field of Classification Search
CPC ...... G01N 33/48; G01N 33/49; G01N 33/723; G01N 33/725; G01N 2333/908; C07C 49/86; C12Q 2326/00; C12Q 1/28; Y10T 436/10; Y10T 436/105831; Y10T 436/206664; Y10T 436/25; Y10T 436/25125
USPC .. 436/8, 15, 63, 66, 67, 135, 164, 166, 174, 436/175; 422/430; 435/28
See application file for complete search history.

(56) References Cited

U.S. PATENT DOCUMENTS 4,416,982 A 11/1983 Tsuda et al.
5,043,266 A 8/1991 Dewar et al.
5,384,248 A * 1/1995 Sakata .................... C12Q 1/28 435/11
2005/0042709 A1* 2/2005 Yonehara ............. G01N 33/723 435/25
2007/0134754 A1* 6/2007 Hirai .................... G01N 33/723 435/23
2013/0171676 A1* 7/2013 Murakami ............... C12Q 1/26 435/23

(Continued)

FOREIGN PATENT DOCUMENTS

EP 0 121 254 A2 10/1984
EP 0 296 752 B1 3/1992
EP 1 238 099 A2 9/2002

(Continued)

OTHER PUBLICATIONS

English translation of the International Search Report for International Application No. PCT/JP2021/033235, dated Oct. 26, 2021.

(Continued)

*Primary Examiner* — Maureen Wallenhorst

(74) *Attorney, Agent, or Firm* — Birch, Stewart, Kolasch & Birch, LLP

(57) ABSTRACT

An object of the present invention is to provide a method for measuring an object to be measured in a specimen by an enzymatic method, the measurement method being able to suppress the positive influence of peroxide derived from the specimen. More specifically, an object of the present invention is to provide a measurement method and a measurement reagent that can suppress elevation in value regardless of whether or not the specimen is a catalase-free specimen. Provided is a measurement method that can accurately quantify hydrogen peroxide derived from an object to be measured, without influence derived from a specimen, by contacting the specimen with an enzyme in the presence of at least one compound selected from the group consisting of a compound represented by the following general formula (I), a benzimidazole derivative having an electron-donating substituent at position 2, and histidine, wherein R1 and R2 are the same or different and each represent hydrogen, a linear or branched alkyl group having 1 to 6 carbon atoms and optionally having a substituent, an aryl group optionally having a substituent, or an alkyloxy group having 1 to 6 carbon atoms.

[Formula 1]

(I)

5 Claims, No Drawings

(56) References Cited

U.S. PATENT DOCUMENTS

| | | | |
|---|---|---|---|
| 2013/0288283 | A1 | 10/2013 | Murakami |

FOREIGN PATENT DOCUMENTS

| | | | |
|---|---|---|---|
| JP | 57-83287 | A | 5/1982 |
| JP | 59-183698 | A | 10/1984 |
| JP | 64-21341 | A | 1/1989 |
| JP | 3-103194 | A | 4/1991 |
| JP | 2003-530081 | A | 10/2003 |
| JP | 2007-236234 | A | 9/2007 |
| WO | WO 01/32916 | A2 | 5/2001 |
| WO | WO 2012/081539 | A1 | 6/2012 |

OTHER PUBLICATIONS

International Preliminary Report on Patentability and English translation of the Written Opinion of the International Searching Authority for International Application No. PCT/JP2021/033235, dated Mar. 23, 2023.

Ogata et al., "Mammalian Acatalasemia: The Perspectives of Bioinformatics and Genetic Toxicology," Acta Medica Okayama, vol. 62, No. 6, Dec. 2008, pp. 345-361 (20 pages total).

Ogata, "Acatalasemia," Kawasaki Medical Welfare Society Journal, vol. 5, No. 1, 1995, pp. 19-29, with English abstract.

Partial Supplementary European Search Report for European Application No. 21866847.3, dated Sep. 25, 2024.

Japanese Office Action for Japanese Application No. 2022-548342, dated Aug. 26, 2025, with English translation.

Taiwanese Office Action and Search Report for Taiwanese Application No. 110133776, dated Jun. 24, 2025, with English translation.

Chinese Office Action and Search Report for Chinese Application No. 202180061542.8, dated Nov. 8, 2025, with English translation of the Office Action.

* cited by examiner

METHOD FOR REDUCING MEASUREMENT ERROR

TECHNICAL FIELD

The present invention relates to a method for measuring an object to be measured in a specimen on the basis of an enzymatic method. More specifically, the present invention relates to a measurement method for quantifying an object to be measured by quantifying hydrogen peroxide resulting from the reaction of the object to be measured in a specimen with an enzyme.

RELATED ART

A measurement method for detecting the amounts of components in specimens derived from biological samples such as whole blood, serum, plasma, or urine by use of enzymatic reaction is known in clinical diagnosis. This measurement method is a measurement method referred to as a so-called enzymatic method. The measurement method involves producing hydrogen peroxide through the reaction of a component to be measured in a specimen with an enzyme whose substrate is the component to be measured, allowing a coloring agent to act on the produced hydrogen peroxide in the presence of peroxidase (POD), and detecting color change to quantify the component to be measured.

The measurement of a component to be measured in a specimen derived from a biological sample on the basis of such an enzymatic method is frequently used in continuous measurement using an automatic analyzer because of convenient operation, etc. However, the enzymatic method is susceptible to a component, other than an object to be measured, derived from a biological sample or a reagent and is disadvantageously subject to positive influence which elevates a measurement value above a theoretical value or negative influence which lowers a measurement value below the theoretical value.

For example, a method of eliminating hydrogen peroxide derived from a component other than a component to be measured by the addition of catalase earlier than "main reaction" in which the component to be measured reacts with an enzyme is known as a method for solving the problem of elevation in measurement value caused by hydrogen peroxide derived from a component other than a component to be measured (Patent Literature 1). However, in this method, azide or protease, if contained in a first reagent, may destabilize the catalase.

A surfactant is often used in a measurement reagent for the enzymatic method, for example, in order to control enzyme reactivity or pretreat a specimen. Depending on the type of the surfactant, the surfactant is prone to producing peroxide during preservation of a reagent. In such a case, the peroxide influences main reaction, disadvantageously still causing elevation in measurement value. As a way to address such a problem, a method for preventing the influence of quantification of hydrogen peroxide resulting from an object to be measured on color change, by performing an enzymatic reaction in an aqueous solution containing α-keto acid to eliminate peroxide contained in a component in a reagent is known (Patent Literature 2).

Acatalasia or acatalasemia, or Takahara's disease was discovered by Takahara in 1946 and is autosomal recessive constitutional anomaly that causes near absence of catalase (Non Patent Literatures 1 and 2). No catalase is contained in biological samples from patients with acatalasia or acatalasemia (Non Patent Literatures 1 and 2). In this context, since endogenous catalase is contained in a biological sample from a patient without acatalasia or acatalasemia, patient's own endogenous catalase eliminates endogenous peroxide, if present, in the biological sample from the patient so that color change ascribable to the quantification of hydrogen peroxide resulting from an object to be measured is often not influenced. However, since no catalase is contained in a biological sample from the patient with acatalasia or acatalasemia, endogenous peroxide contained in the biological sample cannot be eliminated in advance. Thus, the endogenous peroxide derived from the biological sample from the patient, if present, has positive influence on color change ascribable to hydrogen peroxide other than hydrogen peroxide derived from an object to be measured in the enzymatic method, disadvantageously resulting in elevation in measurement value.

The inventors of the present application have conducted studies on the positive influence of such endogenous peroxide derived from a biological sample from the patient, using pyruvic acid, an example of α-keto acid disclosed in Patent Literature 2, and consequently found that this approach is capable of suppressing elevation in value in a specimen derived from a biological sample from the patient with an acatalasia or acatalasemia (hereinafter, also simply referred to as a catalase-free specimen), whereas a measured absorbance value is disadvantageously decreased in a specimen derived from a biological sample from a healthy person, or a calibrator or the like (Comparative Examples described in Examples provided hereinbelow). Although the reason therefor is not clear, it has been considered that the α-keto acid may be likely to interfere with the main reaction itself in which hydrogen peroxide attributed to an object to be measured reacts with peroxidase and a coloring agent.

CITATION LIST

Patent Literature

Patent Literature 1: Japanese Patent Laid-Open No. 2007-236234

Patent Literature 2: International Publication No. WO2012/081539

Non Patent Literature

Non Patent Literature 1: Kawasaki Medical Welfare Society Journal, Vol. 5, No. 1, 1995, 19-29

Non Patent Literature 2: Acta Med. Okayama, 2008, Vol. 62, No. 6, 345-361

SUMMARY OF INVENTION

An object of the present invention is to provide a method for measuring an object to be measured in a specimen by an enzymatic method, the measurement method being able to suppress the positive influence of peroxide derived from the specimen. More specifically, an object of the present invention is to provide a measurement method and a measurement reagent that can suppress elevation in value in a catalase-free specimen without influencing a specimen from a healthy person or the color development of a calibrator or the like.

Solution to Problem

The present invention is directed to attaining the objects. For a method for measuring a component to be measured by quantifying hydrogen peroxide produced through the reaction of the component to be measured in a specimen with an enzyme, diligent studies have been made to search for a compound that can suppress elevation in value in a "catalase-free specimen" without influencing a specimen from a healthy person or the color development of a calibrator or the like. As a result, it has been found that hydrogen peroxide derived from an object to be measured can be accurately quantified, without influence derived from a specimen, by contacting the specimen with an enzyme in the presence of at least one compound selected from the group consisting of a compound represented by the following general formula (I), a benzimidazole derivative having an electron-donating substituent at position 2, and histidine, leading to the completion of the present invention:

[Formula 1]

(I)

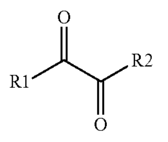

wherein R1 and R2 are the same or different and each represent hydrogen, a linear or branched alkyl group having 1 to 6 carbon atoms and optionally having a substituent, an aryl group optionally having a substituent, or an alkyloxy group having 1 to 6 carbon atoms.

Specifically, the present invention has the following configurations.

<1>

A method for measuring a component to be measured by quantifying hydrogen peroxide produced through the reaction of the component to be measured in a specimen with an enzyme, the measurement method including:

(A) producing hydrogen peroxide by contacting the specimen with the enzyme in the presence of at least one compound selected from the group consisting of a compound represented by the following general formula (I), a benzimidazole derivative having an electron-donating substituent at position 2, and histidine;

(B) reacting the produced hydrogen peroxide with a coloring agent in the presence of peroxidase; and (C) detecting color change:

[Formula 1]

(I)

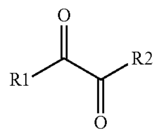

wherein R1 and R2 are the same or different and each represent hydrogen, a linear or branched alkyl group having 1 to 6 carbon atoms and optionally having a substituent, an aryl group optionally having a substituent, or an alkyloxy group having 1 to 6 carbon atoms.

<2>

The measurement method according to <1>, wherein each of R1 and R2 in formula (I) is hydrogen, a linear alkyl group having 1 to 4 carbon atoms, a phenyl group or an alkyloxy group having 1 to 4 carbon atoms.

<3>

The measurement method according to <1>, wherein either one of R1 and R2 in formula (I) is hydrogen or a methyl group, and the other is any selected from the group consisting of hydrogen, a methyl group, an ethyl group, a phenyl group, a methoxy group and an ethoxy group.

<4>

The measurement method according to <1>, wherein the compound represented by formula (I) is phenylglyoxal, glyoxal, diacetyl, 2,3-pentanedione, methyl pyruvate or ethyl pyruvate.

<5>

The measurement method according to <1>, wherein the benzimidazole derivative having an electron-donating substituent at position 2 is 2-aminobenzimidazole.

<6>

The measurement method according to any of <1> to <5>, wherein the component to be measured is HbA1c.

<7>

A measurement reagent including an enzyme that acts on a component to be measured to produce hydrogen peroxide, a coloring agent, peroxidase and at least one compound selected from the group consisting of a compound represented by the following general formula (I), a benzimidazole derivative having an electron-donating substituent at position 2, and histidine:

[Formula 1]

(I)

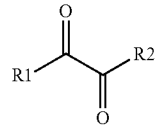

wherein R1 and R2 are the same or different and each represent hydrogen, a linear or branched alkyl group having 1 to 6 carbon atoms and optionally having a substituent, an aryl group optionally having a substituent, or an alkyloxy group having 1 to 6 carbon atoms.

<8>

The measurement reagent according to <7>, wherein each of R1 and R2 in formula (I) is hydrogen, a linear alkyl group having 1 to 4 carbon atoms, a phenyl group or an alkyloxy group having 1 to 4 carbon atoms.

<9>

The measurement reagent according to <7>, wherein either one of R1 and R2 in formula (I) is hydrogen or a methyl group, and the other is any selected from the group consisting of hydrogen, a methyl group, an ethyl group, a phenyl group, a methoxy group and an ethoxy group.

<10>

The measurement reagent according to <5>, wherein the compound represented by formula (I) is phenylglyoxal, glyoxal, diacetyl, 2,3-pentanedione, methyl pyruvate or ethyl pyruvate.

<11>

The measurement reagent according to <7>, wherein the benzimidazole derivative having an electron-donating substituent at position 2 is 2-aminobenzimidazole.

<12>

The measurement reagent according to any of <7> to <11>, wherein the component to be measured is HbA1c, and the enzyme that acts on a component to be measured to produce hydrogen peroxide is protease and fructosyl peptide oxidase.

<13>

A measurement reagent kit including an enzyme that acts on a component to be measured to produce hydrogen peroxide, a coloring agent, peroxidase and at least one compound selected from the group consisting of a compound represented by the following general formula (I), a benzimidazole derivative having an electron-donating substituent at position 2, and histidine, wherein a first reagent includes the at least one compound selected from the group consisting of a compound represented by the following general formula (I), a benzimidazole derivative having an electron-donating substituent at position 2, and histidine, and a second reagent includes the enzyme:

[Formula 1]

(I)

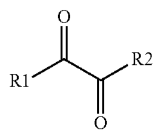

wherein R1 and R2 are the same or different and each represent hydrogen, a linear or branched alkyl group having 1 to 6 carbon atoms and optionally having a substituent, an aryl group optionally having a substituent, or an alkyloxy group having 1 to 6 carbon atoms.

<14>

A method for reducing a measurement error in a method for measuring a component to be measured by circumventing the influence of hydrogen peroxide derived from a component other than the component to be measured contained in a specimen, and quantifying hydrogen peroxide derived from the component to be measured by an enzymatic method, including the step of contacting the specimen with at least one compound selected from the group consisting of a compound represented by the following general formula (I), a benzimidazole derivative having an electron-donating substituent at position 2, and histidine:

[Formula 1]

(I)

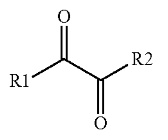

wherein R1 and R2 are the same or different and each represent hydrogen, a linear or branched alkyl group having 1 to 6 carbon atoms and optionally having a substituent, an aryl group optionally having a substituent, or an alkyloxy group having 1 to 6 carbon atoms.

Advantageous Effects of Invention

According to the present invention, in a measurement method based on an enzymatic method that measures a component to be measured by reacting a coloring agent with hydrogen peroxide produced through the reaction of the component to be measured in a specimen with an enzyme, the hydrogen peroxide derived from the object to be measured can be accurately quantified, without the influence of a specimen-derived component other than the object to be measured, by performing the enzymatic reaction in the presence of a specific compound. Particularly, the present invention can provide a measurement method and a measurement reagent that can suppress elevation in value derived from a component other than a component to be measured in a catalase-free specimen without influencing a specimen other than the catalase-free specimen or the color development of the component to be measured such as a calibrator. Specifically, the present invention enables more accurate measurement of a component to be measured by an enzymatic method, without the influence of a specimen-derived component other than the component to be measured, regardless of whether or not the specimen is a catalase-free specimen.

Description of Embodiments (Measurement Method)

The measurement method of the present invention is a method for measuring a component to be measured by quantifying hydrogen peroxide produced through the reaction of the component to be measured in a specimen with an enzyme, the measurement method including the steps of:

(A) producing hydrogen peroxide by contacting the specimen with a reagent containing the enzyme in the presence of at least one specific compound selected from the group consisting of a compound represented by the following general formula (I), a benzimidazole derivative having an electron-donating substituent at position 2, and histidine;

(B) reacting the produced hydrogen peroxide with a coloring agent in the presence of peroxidase; and (C) detecting color change:

[Formula 1]

(I)

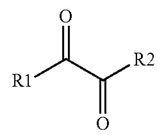

wherein R1 and R2 are the same or different and each represent hydrogen, a linear or branched alkyl group having 1 to 6 carbon atoms and optionally having a substituent, an aryl group optionally having a substituent, or an alkyloxy group having 1 to 6 carbon atoms.

The reaction of the component to be measured with an enzyme that acts on a component to be measured to produce hydrogen peroxide, which is performed by contacting the specimen with the enzyme in the presence of the specific compound, in step (A) can be performed under any reaction condition as long as the condition permits production of hydrogen peroxide. The reaction condition involves, for example, 10 to 50° C., preferably 20 to 40° C., for a reaction time of 5 seconds to 60 minutes, preferably 30 seconds to 15 minutes, more preferably 1 minute to 10 minutes, most preferably 3 to 5 minutes.

The concentration of the specific compound in this reaction can be any concentration that can reduce a measurement error by circumventing the influence of hydrogen peroxide derived from a component other than the component to be measured contained in a specimen. Specifically, the concentration can be 0.001 to 1 v/v % and is preferably 0.01 to 0.5 v/v %, more preferably 0.05 to 0.3 v/v %, in a solution in which the reaction is performed.

The concentration of the specific compound in a formulated measurement reagent can be set to the concentration described above in a solution in which the reaction is performed.

The coloring agent in step (B) can react with hydrogen peroxide in the presence of peroxidase to produce a dye. Examples of the coloring agent include oxidative coupling-type chromogens and leuco-type chromogens.

The leuco-type chromogen is a substance that is converted alone to a dye in the presence of hydrogen peroxide and peroxidase.

Examples of the leuco-type chromogen include phenothiazine chromogens, triphenylmethane chromogens, diphenylamine chromogens, o-phenylenediamine, hydroxypropionic acid, diaminobenzidine, and tetramethylbenzidine. A phenothiazine chromogen is preferred.

Examples of the phenothiazine chromogen include 10-N-carboxymethylcarbamoyl-3,7-bis(dimethylamino)-10H-phenothiazine (CCAP), 10-N-methylcarbamoyl-3,7-bis(dimethylamino)-10H-phenothiazine (MCDP), and 10-N-(carboxymethylaminocarbonyl)-3,7-bis(dimethylamino)-10H-phenothiazine sodium salt (DA-67). The phenothiazine chromogen is particularly preferably 10-N-(carboxymethylaminocarbonyl)-3,7-bis(dimethylamino)-10H-phenothiazine sodium salt (DA-67).

Examples of the triphenylmethane chromogen include N,N,N',N',N'',N''-hexa(3-sulfopropyl)-4,4',4''-triaminotriphenylmethane (TPM-PS).

Examples of the diphenylamine chromogen include N-(carboxymethylaminocarbonyl)-4,4'-bis(dimethylamino)diphenylamine sodium salt (DA-64), 4,4'-bis(dimethylamino)diphenylamine, and bis[3-bis(4-chlorophenyl)methyl-4-dimethylaminophenyl]amine (BCMA).

The oxidative coupling-type chromogen is a substance that produces a dye through the oxidative coupling of two compounds in the presence of hydrogen peroxide and a peroxidatively active substance. Examples of the combination of the two compounds include combinations of couplers and anilines (Trinder reagents), and combinations of couplers and phenols.

Examples of the coupler include 4-aminoantipyrine (4-AA) and 3-methyl-2-benzothiazolinone hydrazine.

Examples of the aniline include N-(3-sulfopropyl)aniline, N-ethyl-N-(2-hydroxy-3-sulfopropyl)-3-methylaniline (TOOS), N-ethyl-N-(2-hydroxy-3-sulfopropyl)-3,5-dimethylaniline (MAOS), N-ethyl-N-(2-hydroxy-3-sulfopropyl)-3,5-dimethoxyaniline (DAOS), N-ethyl-N-(3-sulfopropyl)-3-methylaniline (TOPS), N-(2-hydroxy-3-sulfopropyl)-3,5-dimethoxyaniline (HDAOS), N,N-dimethyl-3-methylaniline, N,N-bis(3-sulfopropyl)-3,5-dimethoxyaniline, N-ethyl-N-(3-sulfopropyl)-3-methoxyaniline, N-ethyl-N-(3-sulfopropyl)aniline, N-ethyl-N-(3-sulfopropyl)-3,5-dimethoxyaniline, N-(3-sulfopropyl)-3,5-dimethoxyaniline, N-ethyl-N-(3-sulfopropyl)-3,5-dimethylaniline, N-ethyl-N-(2-hydroxy-3-sulfopropyl)-3-methoxyaniline, N-ethyl-N-(2-hydroxy-3-sulfopropyl)aniline, N-ethyl-N-(3-methylphenyl)-N'-succinylethylenediamine (EMSE), N-ethyl-N-(3-methylphenyl)-N'-acetylethylenediamine, and N-ethyl-N-(2-hydroxy-3-sulfopropyl)-4-fluoro-3,5-dimethoxyaniline (F-DAOS).

Examples of the phenol include phenol, 4-chlorophenol, 3-methylphenol, and 3-hydroxy-2,4,6-triiodobenzoic acid (HTIB).

The color change of the produced dye in step (C) can be detected by the measurement of absorbance. Examples of the measurement of absorbance include a measurement method using a spectrophotometer.

The color change can be calculated as a concentration by applying the absorbance measured in step (C) to a calibration curve that is prepared using a component to be measured at known concentrations and represents the relationship between the concentration of the component to be measured and the absorbance.

The measurement method of the present invention can circumvent positive influence derived from a component other than the component to be measured in a specimen, and accurately quantify hydrogen peroxide derived from the object to be measured. Examples of the component other than the component to be measured in a specimen include peroxide that is not derived from the component to be measured in a biological sample, peroxide contained in a measurement reagent, and peroxide resulting from the pretreatment of a biological sample. Since no catalase is contained in a biological sample from a patient with acatalasia or acatalasemia, endogenous peroxide, if present, contained in the biological sample cannot be eliminated in advance, causing positive influence. Therefore, the present invention is particularly preferred because the influence of such endogenous peroxide can be circumvented.

(Sample and Specimen)

The sample for use in the method of the present invention can be any sample derived from a living body. Examples thereof include whole blood, serum, plasma, urine, erythrocytes separated from whole blood, and erythrocytes separated from whole blood and further washed.

The biological sample is used as a specimen for the present measurement method either directly or after being subjected to given pretreatment, dilution, or the like. The pretreatment includes any pretreatment necessary for measuring an object to be measured in the biological sample, such as filtration through a filter, centrifugation, treatment with an anticoagulant, treatment with an antiseptic, and heating or cooling treatment.

(Specific Compound)

Examples of the specific compound of the present invention include compounds of the following 1. to 3.

1. Compound Represented by Following General Formula (I)

[Formula 1]

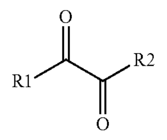

(I)

In formula (I), R1 and R2 are the same or different and each represent hydrogen, a linear or branched alkyl group having 1 to 6 carbon atoms and optionally having a substituent, an aryl group optionally having a substituent, or an alkyloxy group having 1 to 6 carbon atoms.

Examples of the linear or branched alkyl group having 1 to 6 carbon atoms include a methyl group, an ethyl group, a propyl group, an isopropyl group, a butyl group, a tert-butyl group, a pentyl group, and a hexyl group. Specific examples of such a compound include methylglyoxal (R1=hydrogen, R2=a methyl group, CAS Number [78-98-8]), diacetyl (R1=a methyl group, R2=a methyl group, CAS Number [431-03-8]), 2,3-pentanedione (R1=a methyl group, R2=an ethyl group, CAS Number [600-14-6]), 3,4-hexanedione (R1=an ethyl group, R2=an ethyl group, CAS Number [4437-51-8]), 2,3-heptanedione (R1=a methyl group, R2=n-butyl group, CAS Number [96-04-8]), and 5-methyl-2,3-hexanedione (R1=a methyl group, R2=tert-butyl group, CAS Number [13706-86-0]). Among them, a compound wherein R1 and R2 are the same or different and each represent hydrogen, a methyl group, or an ethyl group is preferred. Examples of the substituent include a halogen atom, a methyl group, an amino group, a sulfo group, and a carboxyl group.

Examples of the aryl group include a phenyl group and a naphthyl group. Examples of the substituent include a halogen atom, a methyl group, an amino group, a sulfo group, and a carboxyl group. Specific examples of such a compound include phenylglyoxal (R1=hydrogen, R2=a phenyl group, CAS Number [1075-06-5]), 1-phenyl-1,2-propanedione (R1=a methyl group, R2=a phenyl group, CAS Number [579-07-7]), 1-(4-chlorophenyl)propane-1,2-dione (CAS Number [10557-21-8]), 1-[4-(trifluoromethyl)phenyl]propane-1,2-dione (CAS Number [10557-13-8]), and 1-(4-nitrophenyl)propane-1,2-dione (CAS Number [6159-25-7]). Among them, a compound wherein R1 is hydrogen or a methyl group and R2 is a phenyl group is preferred.

Examples of the alkyloxy group having 1 to 6 carbon atoms include a methoxy group, an ethoxy group, a propoxy group, a butoxy group, a pentoxy group, and a hexoxy group. Specific examples of such a compound include methyl pyruvate (R1=a methyl group, R2=a methoxy group, CAS Number [600-22-6]), methyl 2-oxobutyrate (R1=an ethyl group, R2=a methoxy group, CAS Number [3952-66-7]), ethyl pyruvate (R1=a methyl group, R2=an ethoxy group, CAS Number [617-35-6]), dimethyl oxalate (R1=R2=a methoxy group, CAS Number [553-90-2]), methyl 2-oxovalerate (R1=propyl group, R2=a methoxy group, CAS Number [6376-59-6]), diethyl oxalate (R1=R2=an ethoxy group, CAS Number [95-92-1]), and methyl benzoylformate (R1=a phenyl group, R2=a methoxy group, CAS Number [15206-55-0]). Among them, a compound readily soluble in water is preferred. Particularly, a compound wherein either one of R1 and R2 is hydrogen or a methyl group and the other is a methoxy group or an ethoxy group is preferred.

In the compound represented by formula (I) mentioned above, more preferably, each of R1 and R2 is hydrogen, a linear or branched alkyl group having 1 to 4 carbon atoms, a phenyl group optionally having a substituent, or an alkyloxy group having 1 to 4 carbon atoms. Still more preferably, each of R1 and R2 is hydrogen, a linear or branched alkyl group having 1 to 4 carbon atoms, a phenyl group, or an alkyloxy group having 1 to 4 carbon atoms. More specifically, phenylglyoxal (R1=hydrogen, R2=a phenyl group, CAS Number [1075-06-5])), glyoxal (R1=hydrogen, R2=hydrogen, CAS Number [107-22-2]), diacetyl (R1=a methyl group, R2=a methyl group, CAS Number [431-03-8]), 2,3-pentanedione (R1=a methyl group, R2=an ethyl group, CAS Number [600-14-6]), 1-phenyl-1,2-propanedione (R1=a methyl group, R2=a phenyl group, CAS Number [579-07-7]), methyl pyruvate (R1=a methyl group, R2=a methoxy group, CAS Number [600-22-6]) or ethyl pyruvate (R1=a methyl group, R2=an ethoxy group, CAS Number [617-35-6]) is more preferred, and phenylglyoxal is still more preferred.

2. Benzimidazole Derivative Having Electron-Donating Substituent at Position 2

The benzimidazole derivative having an electron-donating substituent at position 2 of the present invention can be a compound that has a benzimidazole skeleton substituted at position 2 by the substituent, and has an effect of suppressing the positive influence of peroxide derived from a specimen in a method for measuring an object to be measured in the specimen by an enzymatic method.

Examples of the electron-donating substituent bonded to position 2 of the derivative having the effect include an amino group ($-NH_2$ or $-NR_2$ wherein R is an alkyl group), an alkyloxy group, an alkyl group, and an aryl group.

Examples of such a compound include 2-aminobenzimidazole (CAS Number [934-32-7]) having an amino group as the substituent at position 2, and 2-ethyl-1H-benzimidazole (CAS Number [1848-84-6]) having an ethyl group as the substituent at position 2. Among them, 2-aminobenzimidazole is preferred.

3. Histidine

The histidine used in the present invention is a compound defined by CAS Number [71-00-1].

(Component to be Measured)

The enzymatic method according to the present invention is a measurement method which involves producing hydrogen peroxide through the reaction of a component to be measured in a specimen with an enzyme whose substrate is the component to be measured, allowing a coloring agent to act on the produced hydrogen peroxide in the presence of peroxidase (POD), and detecting color change to quantify the component to be measured. Thus, the component to be measured is not particularly limited, and every component that is measurable by quantifying hydrogen peroxide produced through enzymatic reaction can be measured. Examples of the enzyme that reacts with the component to be measured to produce hydrogen peroxide include an enzyme that directly converts the component to be measured to hydrogen peroxide, an enzyme that indirectly converts the component to be measured to hydrogen peroxide, an enzyme that allows the component to be measured to directly produce hydrogen peroxide, and an enzyme that allows the component to be measured to indirectly produce hydrogen peroxide. Thus, every such component measurable through enzymatic reaction is capable of serving as the object to be measured of the present invention.

Specific examples thereof include hemoglobin A1c (HbA1c), glycoalbumin (GA), uric acid, creatinine, cholesterol, triglyceride, polyamine, bile acid, 1,5-anhydroglucitol, pyruvic acid, lactic acid, phospholipid, urea, glucose, choline, creatin, and free fatty acid. Oxidase specific for the component to be measured described above or its derivative will be enumerated below in the form of "component to be measured (enzyme)": hemoglobin A1c (protease, fructosyl amino acid oxidase or fructosyl peptide oxidase), GA (protease or ketoamine oxidase), uric acid (uricase), creatinine (creatininase, creatinase, or sarcosine oxidase), cholesterol (cholesterol oxidase), triglyceride (lipoprotein lipase, glycerol kinase, or glycerol-3-phosphate oxidase), polyamine (polyamine amidohydrolase, polyamine oxidase, or putrescine oxidase), bile acid (3-α-hydroxysteroid dehydrogenase or diaphorase), 1,5-anhydroglucitol (1,5-anhydroglucitol oxidase or pyranose oxidase), pyruvic acid (pyruvate oxidase), lactic acid (lactate oxidase), phospholipid (phospholipase D or choline oxidase), and urea (urea amidolyase, pyruvate kinase, or pyruvate oxidase).

The reaction of the component to be measured with an enzyme that acts on a component to be measured to produce hydrogen peroxide in the measurement method of the present invention is preferably performed in an aqueous medium. Examples of the aqueous medium include deionized water, distilled water, and buffer solutions. The pH of the buffer solution is pH 4.0 to 10.0, preferably pH 6.0 to 8.0. Examples of the buffer for use in the buffer solution include phosphate buffers, borate buffers, and Good's buffers.

The reaction of the component to be measured with the enzyme may be performed in the presence of a stabilizer, an antiseptic, an interfering substance eliminator, a reaction accelerator, or the like.

(Measurement Reagent)

Examples of the measurement reagent configuration for carrying out the measurement method of the present invention include two-reagent and three-reagent kits. Examples of the three reagents include a configuration consisting of a pretreatment liquid for pretreating a sample, a first reagent, and a second reagent. Examples of the two reagents include a configuration consisting of the first reagent and the second reagent.

A coloring agent and POD are respectively contained in separate reagents, and the specific compound component of the present invention is contained in the pretreatment liquid or the first reagent.

Specific aspect of reagent formulations will be given below.

(1) Hemoglobin A1c measurement reagent kit

First reagent: protease, the coloring agent, and the specific compound of the present invention Second reagent: fructosyl peptide oxidase and POD (2) Glycoalbumin measurement reagent kit First reagent: protease, POD, and the specific compound of the present invention Second reagent: ketoamine oxidase and the coloring agent The measurement reagent of the present invention can be applied to various automatic analyzers as is conventionally done. Such application to various automatic analyzers can provide a method for measuring each component to be measured while positive influence derived from a component other than the component to be measured in a specimen is eliminated.

(Measurement Method and Measurement Reagent for Hemoglobin A1c)

The component to be measured of the present invention is not particularly limited, and every component that is measurable by quantifying hydrogen peroxide produced through enzymatic reaction can be measured. The case of particularly measuring hemoglobin A1c among such components will be described.

Examples of the method for measuring HbA1c according to the present invention include a method using a hemoglobin A1c measurement reagent kit including: a first reagent including protease, a coloring agent, and the specific compound of the present invention; and a second reagent including fructosyl peptide oxidase and POD.

First, the first reagent is added to a specimen so that the N-terminal glycated dipeptide of a HbA1c β chain is digested and cleaved with the protease. Subsequently, the second reagent is added so that oxidase specific for the glycated dipeptide (fructosyl peptide oxidase) acts thereon and then, the coloring agent acts on the produced hydrogen peroxide in the presence of the peroxidase, followed by colorimetry. The reaction of the enzyme that acts on a component to be measured to produce hydrogen peroxide is performed in the presence of the specific compound of the present invention contained in the first reagent. As a result, positive influence derived from the component other than the component to be measured can be suppressed.

The hemoglobin A1c is generally determined as HbA1c %. The "HbA1c %" is usually used in clinical practice and means the ratio (5) of an A1c concentration to a hemoglobin concentration in a sample.

The method for measuring HbA1c % basically includes: a first step of optically measuring a hemoglobin concentration in a sample; a second step of optically measuring a HbA1c concentration in the sample; and the step of calculating the ratio (HbA1c %) of the HbA1c concentration to the hemoglobin concentration in the sample. The hemoglobin A1c measurement mentioned above corresponds to the second step of the method for measuring HbA1c %.

In the method for measuring A1c %, the optical measurement of the sample in the first step is performed by measuring absorbance using each of light of a first wavelength and light of a second wavelength. The hemoglobin concentration measured at the first wavelength is corrected using the measurement value obtained at the second wavelength. The hemoglobin concentration thus corrected is used in the HbA1c calculation step.

For the measurement of the hemoglobin concentration, treatment that stabilizes absorbance with hemoglobin as a given structure may be performed by a method known in the art such as conversion to methemoglobin. For the measurement of the HbA1c concentration, treatment that facilitates the digestion and cleavage of the glycated dipeptide from the HbA1c β chain may be performed by the coexistence of a surfactant or the like during the digestion and cleavage with the protease.

In the present specification, the "first wavelength" means a wavelength for measuring hemoglobin and is preferably the wavelength of first light for use in the optical measurement of the hemoglobin concentration in the first step of the method of the present invention. The first wavelength can be appropriately selected from the range of 450 nm to 610 nm.

In the present specification, the "second wavelength" means a wavelength for correcting the apparent hemoglobin concentration measured at the first wavelength to a true hemoglobin concentration, and is preferably the wavelength of second light for use in the optical measurement in the first step of the method of the present invention. The second wavelength can be appropriately selected from the range of 690 nm to 900 nm.

(Method for Reducing Measurement Error)

In short, the measurement method of the present invention can also be regarded as method for reducing a measurement error in a method for measuring a component to be measured by circumventing the influence of hydrogen peroxide derived from a component other than the component to be measured contained in a specimen, and quantifying hydrogen peroxide derived from the component to be measured by an enzymatic method. The method for reducing a measurement error according to the present invention is a method including the step of contacting the specimen with at least one compound selected from the group consisting of a compound represented by the following general formula (I), a benzimidazole derivative having an electron-donating substituent at position 2, and histidine, and each configuration is as mentioned above.

[Formula 1]

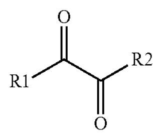

(I)

In formula (I), R1 and R2 are the same or different and each represent hydrogen, a linear or branched alkyl group having 1 to 6 carbon atoms and optionally having a substituent, an aryl group optionally having a substituent, or an alkyloxy group having 1 to 6 carbon atoms.

EXAMPLES

Hereinafter, the present invention will be described in detail with reference to Examples. However, the present invention is not limited by the following Examples.

[Reference Example 1] Preparation of Catalase-Free Model Specimen

Blood A or B collected from each of two healthy persons using an EDTA blood collection tube was centrifuged to obtain blood cells A or B. An aqueous solution of sodium azide known to inhibit catalase activity was added to the blood cells to prepare catalase-free model specimen A or B.

[Example 1] Study Using Catalase-Free Model Specimen

1. Measurement Reagent and Measurement Sample:

<Protease-Containing Substrate Reagent (R1)>

50 mM MES pH 6.0

1.0% Emal 20C (Kao Corp.)

Protin PC10F (Daiwa Kasei Industry Co., Ltd.)

DA-67 (sodium 10-(carboxymethylaminocarbonyl)-3,7-bis(dimethylamino)phenothiazine, FUJIFILM Wako Pure Chemical Corp.)

Additives described in Tables 1 to 4

The manufacturers and distributors of the additives described in Tables 1 to 4 represent the following.

TCI: Tokyo Chemical Industry Co., Ltd.

Kishida: Kishida Chemical Co., Ltd.

Fuji: FUJIFILM Wako Pure Chemical Corp.

<Coloring Reagent (R2)>

50 mM citric acid pH 6.0

Fructosyl peptide oxidase (Kikkoman Corp.)

Peroxidase (Toyobo Co., Ltd.)

<Measurement Sample>

(1) Norudia® N HbA1c calibrators (Sekisui Medical Co., Ltd.) 1 and 2

(2) Catalase-free model specimens A and B prepared in Reference Example 1

2. Operation

The absorbance of HbA1c (5) in each measurement sample was measured according to parameters given below using an automatic analyzer JCA-9130 (JEOL Ltd.) and a combination of reagent R1 and reagent R2 containing various additives shown in Tables 1 to 4. Time setting described below is a setting in which R2 is added approximately 5 minutes after the start of first reaction by the addition of R1.

Parameter:

[HbA1c]

Analysis method: EPA

Calculation method: MSTD

Measurement wavelength (sub/main): HbA1c 805/658

Main DET.P1-P.m-P.n: HbA1c 0-95-98

Sub DET.P.p-P.r: HbA1c 44-47

Reaction time: 10 min

No specimen dilution

Amount of reaction specimen (amount of sample): 6.4 μL

Amount of first reagent (R1): 60 μL, amount of second reagent: 0 μL,

Amount of third reagent (R2): 20 μL, amount of fourth reagent: 0 μL

3. Results

The relative value (%) of the absorbance of HbA1c (%) measured under each condition to the absorbance obtained under condition 1 (additive absent) was calculated and is shown in Tables 1 to 4. The relative value of the measured absorbance of the calibrator 1 or the calibrator 2 is preferably a value close to 100% to that obtained under condition 1. The relative value of the measured absorbance of the catalase-free model specimen A or B is preferably lower than that obtained under condition 1.

TABLE 1

| Measurement results | | | | | | | |
|---|---|---|---|---|---|---|---|
| | | Manufacturer | | Relative value of measured absorbance to that under condition 1 (%) | | Relative value of measured absorbance to that under condition 1 (%) | |
| Condition | Additive | and distributor | Concentration (wt %) | Calibrator 1 | Calibrator 2 | Specimen A | Specimen B |
| 1 | Absent | — | — | 100.0 | 100.0 | 100.0 | 100.0 |
| 2 | Pyruvic acid | TCI | 0.10% | 87.1 | 70.1 | 20.1 | 22.1 |
| 3 | | | 1.0% | 593.2 | 204.3 | 97.7 | 86.2 |
| 4 | 2-Ketoglutaric | TCI | 0.10% | 81.0 | 57.3 | 62.0 | 61.7 |
| 5 | acid | | 1.0% | 895.6 | 292.4 | 164.8 | 146.8 |
| 6 | Levulinic acid | TCI | 0.10% | 89.4 | 81.3 | 132.1 | 127.9 |
| 7 | Phenylglyoxal | TCI | 0.01% | 106.1 | 100.3 | 83.5 | 84.0 |
| 8 | | | 0.10% | 110.4 | 92.4 | 21.0 | 21.6 |
| 9 | | | 0.20% | 109.0 | 80.6 | 17.1 | 17.5 |
| 10 | Glyoxal | TCI | 0.10% | 101.2 | 98.6 | 89.7 | 89.7 |
| 11 | Diacetyl | TCI | 0.01% | 103.2 | 100.5 | 93.7 | 92.9 |
| 12 | | | 0.10% | 116.5 | 100.7 | 59.7 | 58.7 |

TABLE 2

| Measurement results | | | | | | | |
|---|---|---|---|---|---|---|---|
| | | | | Relative value of measured absorbance to that under condition 1 (%) | | Relative value of measured absorbance to that under condition 1 (%) | |
| Condition | Additive | Manufacturer and distributor | Concentration (wt %) | Calibrator 1 | Calibrator 2 | Specimen A | Specimen B |
| 1 | Absent | — | — | 100.0 | 100.0 | 100.0 | 100.0 |
| 13 | Imidazole | Kishida | 0.01% | 101.4 | 98.5 | 100.3 | 100.5 |
| 14 | | | 0.10% | 101.9 | 86.5 | 92.9 | 92.1 |
| 15 | | | 0.20% | 54.8 | 78.2 | 110.8 | 109.3 |
| 16 | Benzimidazole | Kishida | 0.01% | 83.3 | 101.1 | 97.9 | 97.1 |
| 17 | | | 0.10% | 66.4 | 68.8 | 76.4 | 75.2 |
| 18 | | | 0.20% | 63.1 | 50.5 | 56.2 | 55.3 |
| 19 | 2- | Fuji | 0.01% | 106.6 | 111.1 | 85.2 | 86.0 |
| 20 | Aminobenzimidazole | | 0.10% | 120.0 | 99.6 | 55.2 | 55.3 |
| 21 | | | 0.20% | 81.2 | 82.5 | 47.2 | 47.8 |

TABLE 3

| Measurement results | | | | | | | |
|---|---|---|---|---|---|---|---|
| | | | | Relative value of measured absorbance to that under condition 1 (%) | | Relative value of measured absorbance to that under condition 1 (%) | |
| Condition | Additive | Manufacturer and distributor | Concentration (wt %) | Calibrator 1 | Calibrator 2 | Specimen A | Specimen B |
| 1 | Absent | — | — | 100.0 | 100.0 | 100.0 | 100.0 |
| 22 | Methionine | Kishida | 0.10% | 113.8 | 105.4 | 105 | 106.9 |
| 23 | Tryptophan | TCI | 0.10% | 104.9 | 112.6 | 96.6 | 96.4 |
| 24 | L-Histidine | Kishida | 0.10% | 94.5 | 93.4 | 91.7 | 92.0 |
| 25 | | | 0.20% | 86.9 | 88.3 | 82.5 | 83.6 |

TABLE 4

| Measurement | | | | | | | |
|---|---|---|---|---|---|---|---|
| | | | | Relative value of measured absorbance to that under condition 1 (%) | | Relative value of measured absorbance to that under condition 1 (%) | |
| Condition | Additive | Manufacturer and distributor | Concentration (wt %) | Calibrator 1 | Calibrator 2 | Specimen A | Specimen B |
| 1 | Absent | — | — | 100.0 | 100.0 | 100.0 | 100.0 |
| 30 | 2,3-Pentanedione | TCI | 0.01% | 101.6 | 100.4 | 93.8 | 93.1 |
| 31 | | | 0.03% | 106.8 | 101.8 | 76.6 | 75.4 |
| 32 | | | 0.05% | 110.9 | 102.6 | 65.9 | 63.8 |
| 33 | 1-Phenyl-1,2-propanedione | TCI | 0.01% | 103.9 | 100.8 | 91.7 | 90.6 |
| 34 | Methyl pyruvate | TCI | 0.10% | 104.5 | 98.7 | 41.4 | 39.3 |
| 35 | | | 0.01% | 100.4 | 100.8 | 87.6 | 86.1 |
| 36 | Ethyl pyruvate | TCI | 0.10% | 102.2 | 99.3 | 57.1 | 54.6 |
| 37 | | | 0.01% | 100.7 | 100.3 | 92.9 | 92.0 |
| 38 | 2-Ethyl-1H-benzimidazole | TCI | 0.01% | 101.4 | 100.6 | 94.7 | 94.9 |
| 39 | 2-Aminoimidazole | TCI | 0.10% | 136.8 | 120.9 | 102.5 | 102.4 |
| 40 | sulfate | | 0.01% | 104.7 | 102.6 | 100.7 | 99.9 |

3-1. Compound Represented by General Formula (I)

Under condition 2 where 0.10% of pyruvic acid, α-keto acid described in Patent Literature 2, was added, the relative absorbance values of the catalase-free model specimens were decreased to 20.1 to 22.1%, whereas the relative absorbance values of the calibrators 1 and 2 were also decreased to 70.1 to 87.1%, revealing influence on main reaction. Under condition 3 where 1.0% of pyruvic acid was added, the relative absorbance values of the catalase-free model specimens were decreased to 86.2 to 97.7%, whereas the relative absorbance values of the calibrators were 204.3 to 593.2%, suggesting that abnormality occurred in color reaction. Under conditions 4 and 5 where 2-ketoglutaric acid, an analogous compound of α-keto acid, was added, behavior similar to that obtained with pyruvic acid was exhibited. Under condition 6 where levulinic acid (3-acetylpropionic acid) was added, the relative absorbance values of the calibrators were decreased, whereas the relative absorbance values of the catalase-free model specimens were increased, suggesting that abnormality occurred in color reaction.

On the other hand, under condition 8 using 0.10% of phenylglyoxal, a compound found in the present application, the relative absorbance values of the catalase-free model specimens were decreased to 21.0 to 21.6%, whereas the relative absorbance values of the calibrators 1 and 2 were kept at 92.4 to 110.4%. Under condition 9 using 0.20% of phenylglyoxal, the relative absorbance values of the catalase-free model specimens were decreased to 17.1 to 17.5%, whereas the relative absorbance values of the calibrators 1 and 2 were kept at 80.6 to 109.0%. Under condition 7 where 0.01% of phenylglyoxal was added, only the absorbance of the catalase-free model specimens was also decreased without decrease in the absorbance of the calibrators. Particularly, the relative absorbance values of the catalase-free model specimens under conditions 8 and 9 were equivalent to those under condition 2, though conditions 8 and 9 were superior to condition 2 in that the relative absorbance values of the calibrators 1 and 2 were maintained.

Likewise, as for glyoxal (condition 10), diacetyl (conditions 11 and 12), 2,3-pentanedione (conditions 30, 31 and 32), 1-phenyl-1,2-propanedione (condition 33), methyl pyruvate (conditions 34 and 35), and ethyl pyruvate (conditions 36 and 37) having the chemical structure represented by the general formula (I), the relative absorbance values of the catalase-free model specimens were also decreased, whereas the relative absorbance values of the calibrators 1 and 2 were maintained.

Thus, the compound group having the structure of the general formula (I) was found to be a compound that has the functions, intended by the present invention, of specifically eliminating endogenous peroxide in a specimen, while not influencing main reaction attributed to hydrogen peroxide generated from a substance to be measured.

3-2. Benzimidazole Derivative Having Electron-Donating Substituent at Position 2

Conditions 13 to 21 and 38 to 40 will be discussed. In the case of adding imidazole, 0.01% (condition 13) caused no change in absorbance for any of the calibrators and the catalase-free model specimens. In the case of adding 0.1 to 0.21 (conditions 14 and 15), the rate of decrease in the relative absorbance values of the calibrators was larger than that of decrease in the relative absorbance values of the catalase-free model specimens, suggesting that these concentrations are unsuitable for measurement. In the case of adding 0.013 to 0.2% of benzimidazole (conditions 16 to 18), all the concentrations decreased the relative absorbance values of the catalase-free model specimens and however, more decreased the relative absorbance values of the calibrators, exhibiting behavior similar to that obtained with imidazole. On the other hand, in the case of adding 0.01% to 0.2% of 2-aminobenzimidazole found in the present application (conditions 19 to 21), all the concentrations significantly decreased the relative absorbance values of the catalase-free model specimen compared with the relative absorbance values of the calibrators. In the case of adding 0.01% of 2-ethyl-1H-benzimidazole (condition 38), the relative absorbance values of the calibrators were also kept at 100.6 to 101.4%, whereas the relative absorbance values of the specimens were decreased. Thus, this compound was found to have the functions intended by the present invention. As for 2-aminoimidazole sulfate (conditions 39 and 40), the relative absorbance values of the specimens were not decreased, suggesting that a benzimidazole skeleton is necessary for a compound having the functions of the present invention.

Thus, the benzimidazole derivative having an electron-donating substituent at position 2 was found to be a compound that has the functions, intended by the present invention, of specifically eliminating endogenous peroxide in a specimen, while not influencing main reaction attributed to hydrogen peroxide generated from a substance to be measured.

3-3. Histidine

Conditions 22 to 25 will be discussed. Under condition 22 where 0.1% of methionine was added and condition 23 where 0.1% of tryptophan was added, the relative absorbance values of the catalase-free model specimens were rarely changed. On the other hand, under conditions 24 and 25 where L-histidine was added, the relative absorbance values of the catalase-free model specimens were decreased, and the rate of this decrease was larger than that of decrease in the relative absorbance values of the calibrators.

Thus, histidine among amino acids was found to be a compound having the functions intended by the present invention.

4. Assessment Results

Further, results of assessing the relative values shown in Tables 1 to 4 are shown in Table 5.

Evaluation criteria were as follows.

4-1. Evaluation Criteria for Calibrator

- A: Both the relative values of the measured absorbance of the calibrators 1 and 2 are 90 to 110%.
- B: Both the relative values of the measured absorbance of the calibrators 1 and 2 are 80 to 120%.
- C: One of the relative values of the measured absorbance of the calibrators 1 and 2 is less than 80% or larger than 120%.

Since the relative values of the measured absorbance of the calibrators 1 and 2 are preferably values close to 100% to that obtained in the absence of an additive, it was concluded that A was most preferred, B was next-preferred, and C was not preferred.

4-2. Evaluation Criteria for Specimen

Under conditions where the calibrator was assessed as A or B, evaluation criteria were as follows.

- A: Both the relative values of the specimens A and B are 60% or less.
- B: Both the relative values of the specimens A and B are 90% or less.
- C: Both the relative values of the specimens A and B are 95% or less.
- D: Both the relative values of the specimens A and B are larger than 95% s.

Since the relative values of the measured absorbance of the catalase-free model specimens A and B are preferably lower than that obtained under condition 1, it was concluded that A was most preferred, B was next-preferred, followed by C, and D did not meet the required performance. Results about a calibrator assessed as "C" were excluded from the specimen evaluation (indicated by "-" in the tables).

4-3. Criteria of Comprehensive Evaluation

Comprehensive evaluation criteria were as follows on the basis of the evaluation of the calibrators and the specimens.

- A: Both the calibrators and the specimens are evaluated as A.
- B: The calibrators are given A and the specimens are given B, or the calibrators are given B and the specimens are given A or B.

C: The calibrators are given A or B and the specimens are given C.

D: The calibrators are given C or the specimens are given D.

It was concluded in the comprehensive evaluation that A was most preferred, B was next-preferred, followed by C, and D was not effective. Condition 14 was supposed to be given C in the comprehensive evaluation according to the criteria and however, given D in the comprehensive evaluation because the relative values of the specimens A and B were higher than that of the calibrator 2.

4-4. Discussion

From Table 5, phenylglyoxal, methyl pyruvate, and ethyl pyruvate involving comprehensive evaluation A are most preferred compounds. Glyoxal, diacetyl, 2-aminobenzimidazole, histidine, and 2,3-pentanedione involving evaluation B are preferred compounds.

These results demonstrated that the compound represented by the general formula (I), the benzimidazole derivative having an electron-donating substituent at position 2, or histidine, found in the present invention, specifically eliminates endogenous peroxide in a specimen, while not influencing main reaction attributed to hydrogen peroxide generated from a component to be measured, by the presence thereof in a measurement system in a method for measuring a component to be measured in a specimen by an enzymatic method.

[Reference Example 2] Measurement of Healthy Person Specimen and Acatalasia Specimen Blood C or D collected from each of two healthy persons using an EDTA blood collection tube, or acatalasia specimen E was centrifuged to obtain blood cells C, D or E.

The blood cells C, D or E were further evaluated by HPLC (Tosoh G11), a measurement method unsusceptible to the presence or absence of catalase. HbA1c (%) was healthy specimen C: 4.95%, healthy specimen D: 6.50%, and catalase-free specimen E: 6.20%.

[Example 2] Study Using Catalase-Free Specimen

1. Measurement Reagent

<Protease-Containing Substrate Reagent (R1-A)>

50 mM MES pH 6.0

1.0% Emal 20C (Kao Corp.)

Protin PC10F (Daiwa Kasei Industry Co., Ltd.)

DA-67 (sodium 10-(carboxymethylaminocarbonyl)-3,7-bis(dimethylamino)phenothiazine, FUJIFILM Wako Pure Chemical Corp.)

<Protease-Containing Substrate Reagent (R1-B)>

50 mM MES pH 6.0

1.0% Emal 20C (Kao Corp.)

Protin PC10F (Daiwa Kasei Industry Co., Ltd.)

DA-67 (sodium 10-(carboxymethylaminocarbonyl)-3,7-bis(dimethylamino)phenothiazine, FUJIFILM Wako Pure Chemical Corp.)

0.10% phenylglyoxal

TABLE 5

Results of evaluating each compound

| | Condition | Concentration (wt %) | Additive | Calibrator evaluation | Specimen evaluation | Comprehensive evaluation | |
|---|---|---|---|---|---|---|---|
| | 1 | — | Absent | — | — | — | |
| Compound (I)-related | 2 | 0.10% | Pyruvic acid | C | — | D | Comparative Example |
| | 3 | 1.0% | | C | — | D | Comparative Example |
| | 4 | 0.10% | 2-Ketoglutaric acid | C | — | D | Comparative Example |
| | 5 | 1.0% | | C | — | D | Comparative Example |
| | 6 | 0.10% | Levulinic acid | B | D | D | Comparative Example |
| | 7 | 0.01% | Phenylglyoxal | A | B | B | Example |
| | 8 | 0.10% | | B | A | B | Example |
| | 9 | 0.20% | | A | A | A | Example |
| | 10 | 0.10% | Glyoxal | A | B | B | Example |
| | 11 | 0.01% | Diacetyl | A | C | C | Example |
| | 12 | 0.10% | | B | A | B | Example |
| Benzimidazole-related | 13 | 0.01% | Imidazole | A | D | D | Comparative Example |
| | 14 | 0.10% | | B | C | D | Comparative Example |
| | 15 | 0.20% | | C | — | D | Comparative Example |
| | 16 | 0.01% | Benzimidazole | B | D | D | Comparative Example |
| | 17 | 0.10% | | C | — | D | Comparative Example |
| | 18 | 0.20% | | C | — | D | Comparative Example |
| | 19 | 0.01% | 2-Aminobenzimidazole | B | B | B | Example |
| | 20 | 0.10% | | B | A | B | Example |
| | 21 | 0.20% | | B | A | B | Example |
| Histidine-related | 22 | 0.10% | Methionine | B | D | D | Comparative Example |
| | 23 | 0.10% | Tryptophan | B | D | D | Comparative Example |
| | 24 | 0.10% | L-Histidine | B | C | C | Example |
| | 25 | 0.20% | | B | B | B | Example |
| Compound (I)-related | 30 | 0.01% | 2,3-Pentanedione | A | C | C | Example |
| | 31 | 0.03% | | A | B | B | Example |
| | 32 | 0.05% | | B | B | B | Example |
| | 33 | 0.01% | 1-Phenyl-1,2-propanedione | A | C | C | Example |
| | 34 | 0.10% | Methyl pyruvate | A | A | A | Example |
| | 35 | 0.01% | | A | B | B | Example |
| | 36 | 0.10% | Ethyl pyruvate | A | A | A | Example |
| | 37 | 0.01% | | A | C | C | Example |
| Benzimidazole-related | 38 | 0.01% | 2-Ethyl-1H—benzimidazole | A | C | C | Example |
| | 39 | 0.10% | 2-Aminoimidazole | C | — | D | Comparative Example |
| | 40 | 0.01% | sulfate | A | D | D | Comparative Example |

<Coloring Reagent (R2)>

50 mM citric acid pH 6.0

Fructosyl peptide oxidase (Kikkoman Corp.)

Peroxidase (Toyobo Co., Ltd.)

2. Test Sample

<Calibrator>

Norudia® N HbA1c calibrators were used.

<Diluent>

Purified water was used.

<Measurement Sample>

The Normal specimens C and D and the catalase-free specimen E prepared in Reference Example 2 were each diluted 26-fold with purified water and then measured.

2. Operation

Each test sample was measured according to parameters given below using an automatic analyzer JCA-9130 (JEOL Ltd.) and a combination of reagent R1-A and reagent R2 or reagent R1-B and reagent R2, and HbA1c (%) was calculated.

Parameter:

[HbA1c and Hb]

Analysis method: EPA

Calculation method: MSTD

Measurement wavelength (sub/main): HbA1c 805/658, Hb 805/478

Main DET.Pl-P.m-P.n: HbA1c 0-95-98, Hb 0-44-47

Sub DET.P.p-P.r: HbA1c 44-47, Hb 0-0

Reaction time: 10 min

No specimen dilution

Amount of reaction specimen (amount of sample): 6.4 μL

Amount of first reagent (R1): 60 μL, amount of second reagent: 0 μL,

Amount of third reagent (R2): 20 μL, amount of fourth reagent: 0 μL

3. Results

Results of measurement using R1-A (additive absent) or R1-B (supplemented with phenylglyoxal) as the first reagent are shown in Table 6. In the case of using the R1-A reagent, the healthy specimens C and D were able to be accurately measured, whereas the catalase-free specimen E exhibited drastic increase in value, that is, increase to 15.46%, compared with an HPLC measurement value of 6.20%. On the other hand, in the case of using the R1-B reagent supplemented with 0.10% of phenylglyoxal found in the present invention, the measurement value of the catalase-free specimen was 6.84%, compared with an HPLC value of 6.20% and was thus able to be measured with much higher accuracy than that of the R1-A reagent containing no additive. In the case of using the R1-B reagent, the healthy specimen C exhibited 5.29%, compared with an HPLC value of 4.95%, and the healthy specimen D exhibited 6.65%, compared with an HPLC value of 6.50%. Thus, slight elevation in value was seen. This is presumably a measurement error resulting from use of the calibrators optimized for the R1-A reagent in calibration with the R1-B reagent. Thus, more highly accurate measurement is considered possible by optimizing another calibrator for the R1-B reagent.

TABLE 6

| | Measurement value of HbA1c (%) | | |
|---|---|---|---|
| | Comparative Example 2 | R1-A Additive absent | Supplemented with phenylglyoxal |
| Healthy specimen C | 4.95 | 4.97 | 5.29 |
| Healthy specimen D | 6.50 | 6.48 | 6.65 |
| Catalase-free specimen E | 6.20 | 15.46 | 6.84 |

INDUSTRIAL APPLICABILITY

The present invention can provide a measurement method and a measurement reagent that can accurately quantify hydrogen peroxide derived from an object to be measured, without the influence of a specimen-derived component other than the object to be measured, in a measurement method based on an enzymatic method. Particularly, the present invention enables more accurate measurement of an object to be measured by an enzymatic method, without the influence of a specimen-derived component other than the object to be measured, regardless of whether or not the specimen is a catalase-free specimen.

The invention claimed is:

1. A method for measuring a component to be measured by quantifying hydrogen peroxide produced through a reaction of the component to be measured in a specimen with an enzyme, the measurement method comprising:

(A) producing hydrogen peroxide by contacting the specimen with the enzyme in the presence of phenylglyoxal;

(B) reacting the produced hydrogen peroxide with a coloring agent in the presence of peroxidase;

(C) detecting color change; and (D) correlating the color change to an amount of hydrogen peroxide; (I)

wherein the component to be measured is HbA1c.

2. A measurement reagent comprising an enzyme that acts on a component to be measured to produce hydrogen peroxide, a coloring agent, peroxidase and (I) phenylglyoxal;

wherein the component to be measured is HbA1c.

3. The measurement reagent according to claim 2, wherein the enzyme that acts on a component to be measured to produce hydrogen peroxide is protease and fructosyl peptide oxidase.

4. A measurement reagent kit comprising an enzyme that acts on a component to be measured to produce hydrogen peroxide, a coloring agent, peroxidase and phenylglyoxal, at least one compound, the kit comprising: a first reagent and a second reagent wherein the first reagent comprises phenylglyoxal;

the second reagent comprises the enzyme; (I)

and wherein the coloring agent and the peroxidase are contained in the first reagent, the second reagent, or a third reagent; and wherein the component to be measured is HbA1c.

5. A method for reducing a measurement error in a method for measuring a component to be measured by circumventing an influence of hydrogen peroxide derived from a component other than the component to be measured contained in a specimen, and quantifying hydrogen peroxide derived from the component to be measured by an enzymatic method, comprising:

(A) contacting the specimen with an enzyme that acts on the component to be measured to produce hydrogen peroxide in the presence of (I) phenylglyoxal;

(B) reacting the hydrogen peroxide produced in step (A) with a coloring agent in the presence of peroxidase;

(C) detecting a color change resulting from the reaction in step (B); and (D) correlating the color change to an amount of hydrogen peroxide, thereby reducing the measurement error by circumventing the influence of hydrogen peroxide derived from a component other than the component to be measured;

wherein the component to be measured is HbA1c.

* * * * *